United States Patent
Yoshida et al.

(10) Patent No.: US 11,203,530 B2
(45) Date of Patent: Dec. 21, 2021

(54) METHOD FOR PRODUCING HEXAGONAL PLATE-SHAPED ZINC OXIDE

(71) Applicant: SAKAI CHEMICAL INDUSTRY CO., LTD., Sakai (JP)

(72) Inventors: Ryohei Yoshida, Fukushima (JP); Mitsuo Hashimoto, Fukushima (JP); Kazutaka Murai, Fukushima (JP)

(73) Assignee: Sakai Chemical Industry Co., Ltd., Osaka (JP)

(*) Notice: Subject to any disclaimer, the term of this patent is extended or adjusted under 35 U.S.C. 154(b) by 12 days.

(21) Appl. No.: 16/615,629

(22) PCT Filed: Jun. 8, 2018

(86) PCT No.: PCT/JP2018/022073
§ 371 (c)(1),
(2) Date: Nov. 21, 2019

(87) PCT Pub. No.: WO2018/230472
PCT Pub. Date: Dec. 20, 2018

(65) Prior Publication Data
US 2020/0172407 A1    Jun. 4, 2020

(30) Foreign Application Priority Data
Jun. 12, 2017   (JP) .............................. JP2017-115411

(51) Int. Cl.
*C01G 9/02*   (2006.01)
*A61K 8/27*   (2006.01)
(Continued)

(52) U.S. Cl.
CPC .................. *C01G 9/02* (2013.01); *A61K 8/27* (2013.01); *A61Q 1/00* (2013.01); *C01G 1/02* (2013.01);
(Continued)

(58) Field of Classification Search
CPC . C01G 9/02; C01G 1/02; C01G 9/003; A61K 8/27; A61Q 1/00
See application file for complete search history.

(56) References Cited

U.S. PATENT DOCUMENTS

| 2014/0050925 A1 | 2/2014 | Sueda et al. |
| 2014/0112862 A1 | 4/2014 | Sueda et al. |

(Continued)

FOREIGN PATENT DOCUMENTS

| CN | 104159850 | 11/2014 |
| JP | 2012-176860 | 9/2012 |

(Continued)

OTHER PUBLICATIONS

Xu, et al., "Controllable morphology evolution of electrodeposited ZnO nano/micro-scale structures in aqueous solution", Materials and Design 30, 2009, pp. 1704-1711.

(Continued)

*Primary Examiner* — James A Fiorito
(74) *Attorney, Agent, or Firm* — Hamre, Schumann, Mueller & Larson, P.C.

(57) ABSTRACT

The present invention provides a method capable of producing hexagonal plate-shaped zinc oxide having a small thickness and a small variation in the particle size. The present invention relates to a method for producing hexagonal plate-shaped zinc oxide, the method including: a step (1) of preparing a slurry mixture containing starting particulate zinc oxide, a zinc acetate solution, and a chloride; and a step (2) of heat aging the slurry mixture obtained in the step (1) at 60° C. to 100° C.

3 Claims, 3 Drawing Sheets

Example 1 ( × 20000)

Example 1 ( × 10000)

(51) Int. Cl.
*A61Q 1/00* (2006.01)
*C01G 1/02* (2006.01)
*C01G 9/00* (2006.01)
*C01D 3/04* (2006.01)

(52) U.S. Cl.
CPC ............... *C01G 9/003* (2013.01); *C01D 3/04* (2013.01); *C01P 2004/01* (2013.01); *C01P 2004/22* (2013.01); *C01P 2004/54* (2013.01)

(56) References Cited

U.S. PATENT DOCUMENTS

| | | |
|---|---|---|
| 2015/0050496 A1 | 2/2015 | Sueda et al. |
| 2016/0319131 A1 | 11/2016 | Sueda et al. |
| 2016/0324742 A1 | 11/2016 | Sueda et al. |
| 2016/0347624 A1 | 12/2016 | Yoshida et al. |

FOREIGN PATENT DOCUMENTS

| | | |
|---|---|---|
| JP | 2014-084256 | 5/2014 |
| JP | 2015-182892 | 10/2015 |
| WO | 2012/147886 | 11/2012 |
| WO | 2015/033990 | 3/2015 |
| WO | 2015/098945 | 7/2015 |
| WO | 2015/098992 | 7/2015 |
| WO | 2015/118777 | 8/2015 |

OTHER PUBLICATIONS

Hong, et al., "Magnetism in Dopant-Free Zno Nanoplates", Nano Letters, 12, 2012, pp. 576-581.

FIG.1
Example 1 (×20000)　　　Example 1 (×10000)

FIG.2
Example 2 (×20000)　　　Example 2 (×10000)

FIG.3
Example 4 (×20000)　　　Example 4 (×10000)

FIG.4

Comparative Example 1 (×20000)

Comparative Example 1 (×10000)

FIG.5

Comparative Example 2 (×20000)

Comparative Example 2 (×10000)

FIG.6

Comparative Example 3 (×20000)

Comparative Example 3 (×10000)

FIG.7

Comparative Example 4 (×20000)

Comparative Example 4 (×10000)

FIG.8

Comparative Example 5 (×10000)

METHOD FOR PRODUCING HEXAGONAL PLATE-SHAPED ZINC OXIDE

TECHNICAL FIELD

The present invention relates to methods for producing hexagonal plate-shaped zinc oxide. Specifically, the present invention relates to a method for producing hexagonal plate-shaped zinc oxide suitable for applications such as cosmetics.

BACKGROUND ART

In recent years, more and more cosmetics have contained components for protecting skin from ultraviolet light and infrared light in sunlight, and various components capable of absorbing or reflecting ultraviolet light and infrared light have been used. For example, zinc oxide is used. Particulate hexagonal plate-shaped zinc oxide or lamellar zinc oxide is more capable of reflecting ultraviolet light and infrared light than amorphous particulate zinc oxide, and is used as a cosmetic component (see Patent Literatures 1 to 4).

CITATION LIST

Patent Literature

Patent Literature 1: WO 2012/147886
Patent Literature 2: WO 2015/118777
Patent Literature 3: JP 2015-182892 A
Patent Literature 4: JP 2012-176860 A

SUMMARY OF INVENTION

Technical Problem

Zinc oxide as a cosmetic component is required to have not only ultraviolet or infrared blocking ability but also excellent texture during use. In order to achieve excellent texture, particulate zinc oxide preferably has a lamellar shape as thin as possible and a small variation in the particle size. Unfortunately, particulate zinc oxide produced by a conventional method for producing hexagonal plate-shaped zinc oxide has a large thickness, and commercially available lamellar zinc oxide has poor particle uniformity. Thus, there is a need to develop a method capable of producing particulate hexagonal plate-shaped zinc oxide having a small thickness, a small variation in the particle size, and excellent texture during use.

The present invention has been made in view of the state of the art and aims to provide a method capable of producing hexagonal plate-shaped zinc oxide having a small thickness and a small variation in the particle size.

Solution to Problem

The present inventors examined a method for producing hexagonal plate-shaped zinc oxide having a small thickness and a small variation in the particle size and found that particulate hexagonal plate-shaped zinc oxide having a small thickness and a small variation in the particle size can be prepared by a production method including preparing a slurry mixture containing starting particulate zinc oxide, a zinc acetate solution, and a chloride and heat aging the resulting slurry mixture at 60° C. to 100° C. Thereby, the present invention has been completed.

That is, one aspect of the present invention relates to a method for producing hexagonal plate-shaped zinc oxide, the method including:
a step (1) of preparing a slurry mixture containing starting particulate zinc oxide, a zinc acetate solution, and a chloride; and
a step (2) of heat aging the slurry mixture obtained in the step (1) at 60° C. to 100° C.

The chloride is preferably present in an amount of 0.3 mol % or more based on the starting particulate zinc oxide used in the step (1) in the slurry mixture obtained in the step (1).

The chloride is preferably at least one selected from sodium chloride, ammonium chloride, and lithium chloride.

The method preferably further includes a step (3) of washing solids obtained from a slurry reaction product produced in the step (2) with water having a temperature from 70° C. to below 100° C.

Another aspect of the present invention relates to hexagonal plate-shaped zinc oxide having an aspect ratio of 4.5 or greater and a ratio D90/D10 of 2.5 or less.

Advantageous Effects of Invention

The method for producing hexagonal plate-shaped zinc oxide of the present invention can produce hexagonal plate-shaped zinc oxide having a small thickness and a small variation in the particle size, and is thus suitable for producing hexagonal plate-shaped zinc oxide for applications for which excellent texture during use is required, such as cosmetics.

DESCRIPTION OF EMBODIMENTS

The following description is offered to specifically describe an embodiment of the present invention. It should be noted that the present invention is not limited only to the following description, and the embodiment can be appropriately modified within the scope of the present invention.
<Method for Producing Hexagonal Plate-Shaped Zinc Oxide>

The method for producing hexagonal plate-shaped zinc oxide of the present invention includes a step (1) of preparing a slurry mixture containing starting particulate zinc oxide, a zinc acetate solution, and a chloride and a step (2) of heat aging the slurry mixture obtained in the step (1) at 60° C. to 100° C.

In the step (1), the starting particulate zinc oxide, the zinc acetate solution, and the chloride may be mixed in any order as long as the slurry containing these is prepared. Specifically, the starting particulate zinc oxide may first be mixed with the zinc acetate solution, followed by mixing with the chloride; or the starting particulate zinc oxide or zinc acetate solution may first be mixed with the chloride, followed by mixing with the rest; or these three components may be simultaneously mixed.

The mixing may be performed by adding any one of the starting particulate zinc oxide, zinc acetate solution, and chloride to the other, or by adding any two or three of the components to a solvent.

In the mixing, each component may be added in one portion or several portions.

In the step (1), the starting particulate zinc oxide, the zinc acetate solution, and the chloride are preferably mixed by stirring to prepare the slurry mixture. The stirring may be performed by any method.

In the step (1), the starting particulate zinc oxide and the chloride each may be subjected to mixing in the form of powder, slurry, or solution. In order to obtain hexagonal plate-shaped zinc oxide having a narrow particle size distribution, each of them is preferably subjected to mixing in the form of slurry or solution.

The slurry and the solution are preferably prepared using water as a solvent.

When the mixing is performed by adding any two or three of the starting particulate zinc oxide, the zinc acetate solution, and the chloride to a solvent, the solvent is preferably water.

When the starting particulate zinc oxide and the chloride are each subjected to mixing in the form of slurry or solution, any amount of a solvent may be used. The amount of the solvent is preferably 1 to 500 ml, more preferably 5 to 100 ml per gram of the starting particulate zinc oxide or chloride.

The zinc acetate solution in the step (1) may contain any solvent as long as zinc acetate is present in solution. The solvent is preferably water. That is, the zinc acetate solution in the step (1) is preferably an aqueous solution of zinc acetate.

The concentration of the zinc acetate solution in the step (1) is preferably 0.1 to 4 mol/l, more preferably 0.3 to 3 mol/l, still more preferably 0.5 to 2 mol/l.

The starting particulate zinc oxide used in the step (1) preferably has a particle size calculated from specific surface area of 0.001 to 1 μm. The starting particulate zinc oxide having such a particle size leads to hexagonal plate-shaped zinc oxide having much better ultraviolet or infrared blocking ability, which is suitable for applications such as cosmetics. The particle size of the starting particulate zinc oxide is more preferably 0.002 to 0.1 μm.

The particle size calculated from specific surface area of the starting particulate zinc oxide corresponds to the diameter of a sphere in which the surface area is equal to the specific surface area determined by the BET method. Specifically, the particle size calculated from specific surface area is a value determined using the following equation:

$$\text{Particle size calculated from specific surface area of starting particulate zinc oxide } (\mu m) = [6/(Sg \times \rho)]$$

($Sg$ (m$^2$/g): specific surface area, $\rho$ (g/cm$^3$): absolute gravity of particle), where $Sg$ is a specific surface area determined with a fully automatic BET specific surface area measuring apparatus Macsorb Model HM-1200 (Mountech Co., Ltd.) and $\rho$ is the absolute gravity of zinc oxide.

The absolute gravity $\rho$ of particle in the calculation is 5.6 which is the absolute gravity of zinc oxide.

In the step (1), the amount of the zinc acetate solution used to prepare the slurry mixture containing starting particulate zinc oxide, a zinc acetate solution, and a chloride is preferably such that the amount of the zinc acetate in the zinc acetate solution is 0.1 to 3 mol per mole of the starting particulate zinc oxide. Use of the zinc acetate solution at such a ratio leads to uniform hexagonal particles. The amount of the zinc acetate solution is more preferably such that the amount of the zinc acetate therein is 0.2 to 1 mol.

The chloride in the step (1) may be any one that leads to the hexagonal plate-shaped zinc oxide, and may be one or more of aluminum chloride, sodium chloride, ammonium chloride, and lithium chloride. In particular, the chloride is preferably at least one selected from sodium chloride, ammonium chloride, and lithium chloride.

The chloride is preferably present in an amount of 0.3 mol % or more based on the starting particulate zinc oxide used in the step (1) in the slurry mixture obtained in the step (1). Use of such an amount of the chloride can lead to particulate hexagonal plate-shaped zinc oxide having a smaller thickness and a more uniform particle size. The amount of the chloride is more preferably 0.4 mol % or more, still more preferably 0.5 mol % or more based on the starting particulate zinc oxide used in the step (1). In order to reduce impurities and in view of productivity, the amount of the chloride in the slurry mixture obtained in the step (1) is preferably 300 mol % or less, more preferably 250 mol % or less, still more preferably 200 mol % or less based on the starting particulate zinc oxide used in the step (1).

The concentration of the zinc acetate in the slurry mixture containing starting particulate zinc oxide, a zinc acetate solution, and a chloride prepared in the step (1) is preferably 0.1 to 3 mol/l, more preferably 0.2 to 1 mol/l.

In the step (1), the slurry containing starting particulate zinc oxide, a zinc acetate solution, and a chloride may be mixed at any temperature. The temperature is preferably 3° C. to 50° C., more preferably 10° C. to 40° C.

In the step (1), the slurry containing starting particulate zinc oxide, a zinc acetate solution, and a chloride may be mixed for any length of time. The length of time may be appropriately set depending on the amounts of the starting materials, and is preferably 1 to 480 minutes, more preferably 30 to 360 minutes.

When the chloride is added to the zinc acetate solution in advance, and the resulting solution is mixed with the starting particulate zinc oxide in the step (1), the length of time to mix the zinc acetate solution containing the chloride with the starting particulate zinc oxide may preferably be, but not limited to, 10 to 420 minutes, more preferably 30 to 300 minutes.

The step (2) is a step of heat aging the slurry mixture obtained in the step (1) at 60° C. to 100° C. The heat aging allows production of uniformly hexagonal plate-shaped particles. The temperature of heating may be 60° C. to 100° C., preferably 70° C. to 100° C., more preferably 80° C. to 100° C., still more preferably 90° C. to 100° C. The slurry mixture may be heat aged under stirring or by allowing to stand. It is preferably heat aged under stirring.

The heat aging in the step (2) may be performed for any length of time. In view of the yield and productivity of the hexagonal plate-shaped zinc oxide, the length of time is preferably 10 to 540 minutes, more preferably 20 to 420 minutes, still more preferably 30 to 300 minutes.

The slurry mixture obtained in the step (1) is preferably heated to 60° C. to 100° C. at a temperature rise rate of 10° C./min or less. Such a temperature rise rate allows enough time to grow crystals and thus can lead to uniform aluminum-doped hexagonal plate-shaped zinc oxide having a small variation in particle size. The temperature rise rate is more preferably 5° C./min or less, still more preferably 3° C./min or less.

The method for producing hexagonal plate-shaped zinc oxide of the present invention preferably further includes a step (3) of washing solids obtained from a slurry reaction product produced in the step (2) with water having a temperature from 70° C. to below 100° C. The step (3) can be performed by stirring solids (cake) obtained by filtering the slurry reaction product produced in the step (2) in water having a temperature from 70° C. to below 100° C. This step allows more sufficient removal of excess salts such as unreacted zinc acetate and thus can lead to uniform hexagonal plate-shaped zinc oxide having a small variation in particle size.

The temperature in the step (3) may range from 70° C. to below 100° C., preferably from 80° C. to below 100° C., more preferably from 90° C. to below 100° C.

The method for producing hexagonal plate-shaped zinc oxide of the present invention may further include filtering and/or washing (with water) after the step (2) (between the steps (2) and (3)) or after the step (3). This step(s) allows removal of excess salts such as unreacted starting materials and thus can lead to high purity hexagonal plate-shaped zinc oxide. The method may further include cooling the liquid before filtering.

The amount of water used for washing after the step (2), after the step (3), or during the step (3) is preferably 1000% by mass or more relative to 100% by mass of the solids to be washed. Such an amount of water allows more sufficient removal of excess salts in the solids.

The length of time of the step (3) may be appropriately set depending on the amounts of the solids and water to be used, and is preferably 10 to 540 minutes, more preferably 30 to 480 minutes.

The method for producing hexagonal plate-shaped zinc oxide of the present invention may further include drying the hexagonal plate-shaped zinc oxide.

The hexagonal plate-shaped zinc oxide may be dried at any temperature as long as the hexagonal plate-shaped zinc oxide is dried. The temperature is preferably 100° C. to 200° C., more preferably 110° C. to 150° C. The hexagonal plate-shaped zinc oxide may be dried for any length of time. The length of time is preferably 6 to 200 hours, more preferably 12 to 170 hours.

The method for producing hexagonal plate-shaped zinc oxide of the present invention may further include additional steps other than the steps (1) to (3), washing, filtering, and drying steps. The additional steps include an optional surface treatment step. The additional steps may be performed before or after any of the steps (1) to (3).

In the method for producing hexagonal plate-shaped zinc oxide of the present invention, each of the steps (1) to (3), washing, filtering, drying, and additional steps may be performed one or more times.

<Hexagonal Plate-Shaped Zinc Oxide>

The hexagonal plate-shaped zinc oxide of the present invention has an aspect ratio of 4.5 or greater and a ratio D90/D10 of 2.5 or less.

The hexagonal plate-shaped zinc oxide of the present invention having such an aspect ratio and a ratio D90/D10 has excellent slippage and texture derived from its shape.

The aspect ratio of the hexagonal plate-shaped zinc oxide of the present invention should be 4.5 or greater, preferably 4.7 or greater, more preferably 5.0 or greater, still more preferably 5.2 or greater. The upper value of the aspect ratio is not limited. The aspect ratio of the hexagonal plate-shaped zinc oxide is usually 100 or less.

The ratio D90/D10 of the hexagonal plate-shaped zinc oxide of the present invention should be 2.5 or less, preferably 2.3 or less, more preferably 2.2 or less.

The hexagonal plate-shaped zinc oxide of the present invention preferably has a median diameter of 0.05 to 5 μm. The hexagonal plate-shaped zinc oxide having such a median diameter exerts an excellent effect of blocking ultraviolet light and infrared light. The median diameter of the hexagonal plate-shaped zinc oxide is more preferably 0.07 to 4 μm, still more preferably 0.08 to 3.5 μm. The median diameter herein is a particle size at which 50% by number of particles are accumulated (D50) and is determined by the method described in EXAMPLES.

The hexagonal plate-shaped zinc oxide of the present invention preferably has a BET specific surface area of 1.1 $m^2/g$ or greater. The hexagonal plate-shaped zinc oxide having such a BET specific surface area has ultraviolet blocking ability and masking ability in preferred ranges. The BET specific surface area is more preferably 2.2 $m^2/g$ or greater, still more preferably 2.3 $m^2/g$ or greater.

The hexagonal plate-shaped zinc oxide of the present invention preferably has a total light transmittance at a wavelength of 350 nm of 60% or lower. The hexagonal plate-shaped zinc oxide having such a total light transmittance has excellent ultraviolet blocking ability. The total light transmittance at a wavelength of 350 nm is more preferably 58% or lower, still more preferably 57% or lower.

The hexagonal plate-shaped zinc oxide of the present invention preferably has a parallel light transmittance at a wavelength of 400 nm of 35% or lower. The hexagonal plate-shaped zinc oxide having such a parallel light transmittance has high masking ability and is thus more suitable for applications in which color is important, such as cosmetics. The parallel light transmittance at a wavelength of 400 nm is more preferably 33% or lower, still more preferably 32% or lower.

The hexagonal plate-shaped zinc oxide of the present invention may be doped with an additional element, and may be subjected to surface treatment, as needed. Non-limiting examples of the surface treatment include inorganic surface treatments for forming an inorganic oxide layer such as a silica layer, an alumina layer, a zirconia layer, or a titania layer and organic surface treatments using an organic silicon compound, an organic aluminum compound, an organic titanium compound, a higher fatty acid, a metal soap, a polyol, or an alkanolamine. The hexagonal plate-shaped zinc oxide may be subjected to two or more surface treatments.

The hexagonal plate-shaped zinc oxide of the present invention having a small thickness and a small variation in the particle size and thus having excellent slippage and texture is suitable for the starting materials of cosmetics.

In addition, it is suitable for applications such as exoergic filler, exoergic resin compositions, exoergic grease, vulcanization accelerators for rubber, pigments for coating material or ink, electronic components such as ferrites and varistors, pharmaceuticals, and films.

EXAMPLES

Hereinafter, the present invention will be described with reference to examples. However, the present invention is not limited to these examples. The terms "%" and "part(s)" represent "% by mass (% by weight)" and "part(s) by mass (part(s) by weight)", respectively, unless otherwise specified.

Example 1

A slurry was obtained by repulping 78.4 g of starting particulate zinc oxide (FINEX-50 available from Sakai Chemical Industry Co., Ltd., particle size calculated from specific surface area: 0.02 μm) with 399 ml of water. Separately, 601 ml of a 1.30 mol/l aqueous solution of zinc acetate was prepared. To the aqueous solution was added 1.15 g of sodium chloride (2 mol % based on the starting particulate zinc oxide). The slurry and the zinc acetate aqueous solution were added simultaneously to 200 ml of water controlled at 30° C. such that the total amounts were added over 120 minutes. Thus, a slurry mixture containing a 0.65 mol/l aqueous solution of zinc acetate, the starting particulate zinc oxide, and the sodium chloride was obtained. Subsequently, the slurry mixture was heated to 95° C. over 65 minutes under stirring, and then aged at 95° C. for two hours under stirring. After the aging, the slurry mixture was immediately cooled and then filtered and washed to obtain a cake. The cake was repulped with water, heated to 95° C., stirred for two hours, filtered, washed (with water), and dried at 20° C. for 16 hours. Thus, particulate hexagonal plate-shaped zinc oxide was obtained.

Example 2

A slurry was obtained by repulping 78.4 g of starting particulate zinc oxide (FINEX-50 available from Sakai Chemical Industry Co., Ltd., particle size calculated from specific surface area: 0.02 μm) with 399 ml of water. Separately, 601 ml of a 1.30 mol/l aqueous solution of zinc acetate was prepared. To the aqueous solution was added 1.05 g of ammonium chloride (2 mol % based on the starting particulate zinc oxide). The slurry and the zinc acetate aqueous solution were added simultaneously to 200 ml of water controlled at 30° C. such that the total amounts were added over 120 minutes. Thus, a slurry mixture containing a 0.65 mol/l aqueous solution of zinc acetate, the starting particulate zinc oxide, and the ammonium chloride was obtained. Subsequently, the slurry mixture was heated to 95° C. over 65 minutes under stirring, and then aged at 95° C. for two hours under stirring. After the aging, the slurry mixture was immediately cooled and then filtered and washed to obtain a cake. The cake was repulped with water, heated to 95° C., stirred for two hours, filtered, washed (with water), and dried at 120° C. for 16 hours. Thus, particulate hexagonal plate-shaped zinc oxide was obtained.

Example 3

A slurry was obtained by repulping 76.8 g of starting particulate zinc oxide (FINEX-50 available from Sakai Chemical Industry Co., Ltd., particle size calculated from specific surface area: 0.02 μm) with 399 ml of water. Separately, 601 ml of a 1.30 mol/l aqueous solution of zinc acetate was prepared. To the aqueous solution was added 2.30 g of sodium chloride (4.2 mol % based on the starting particulate zinc oxide). The slurry and the zinc acetate aqueous solution were added simultaneously to 200 ml of water controlled at 30° C. such that the total amounts were added over 120 minutes. Thus, a slurry mixture containing a 0.65 mol/l aqueous solution of zinc acetate, the starting particulate zinc oxide, and the sodium chloride was obtained. Subsequently, the slurry mixture was heated to 95° C. over 65 minutes under stirring, and then aged at 95° C. for two hours under stirring. After the aging, the slurry mixture was immediately cooled and then filtered and washed to obtain a cake. The cake was repulped with water, heated to 95° C., stirred for two hours, filtered, washed (with water), and dried at 120° C. for 16 hours. Thus, particulate hexagonal plate-shaped zinc oxide was obtained.

Example 4

A slurry was obtained by repulping 64 g of starting particulate zinc oxide (FINEX-50 available from Sakai Chemical Industry Co., Ltd., particle size calculated from specific surface area: 0.02 μm) with 399 ml of water. Separately, 601 ml of a 1.30 mol/l aqueous solution of zinc acetate was prepared. To the aqueous solution was added 11.49 g of sodium chloride (25 mol % based on the starting particulate zinc oxide). The slurry and the zinc acetate aqueous solution were added simultaneously to 200 ml of water controlled at 30° C. such that the total amounts were added over 120 minutes. Thus, a slurry mixture containing a 0.65 mol/l aqueous solution of zinc acetate, the starting particulate zinc oxide, and the sodium chloride was obtained. Subsequently, the slurry mixture was heated to 95° C. over 65 minutes under stirring, and then aged at 95° C. for two hours under stirring. After the aging, the slurry mixture was immediately cooled and then filtered and washed to obtain a cake. The cake was repulped with water, heated to 95° C., stirred for two hours, filtered, washed (with water), and dried at 120° C. for 16 hours. Thus, particulate hexagonal plate-shaped zinc oxide was obtained.

Example 5

A slurry was obtained by repulping 76.8 g of starting particulate zinc oxide (FINEX-50 available from Sakai Chemical Industry Co., Ltd., particle size calculated from specific surface area: 0.02 μm) with 399 ml of water. Separately, 601 ml of a 1.30 mol/l aqueous solution of zinc acetate was prepared. To the aqueous solution was added 1.67 g of lithium chloride (4.2 mol % based on the starting particulate zinc oxide). The slurry and the zinc acetate aqueous solution were added simultaneously to 200 ml of water controlled at 30° C. such that the total amounts were added over 120 minutes. Thus, a slurry mixture containing a 0.65 mol/l aqueous solution of zinc acetate, the starting particulate zinc oxide, and the lithium chloride was obtained. Subsequently, the slurry mixture was heated to 95° C. over 65 minutes under stirring, and then aged at 95° C. for two hours under stirring. After the aging, the slurry mixture was immediately cooled and then filtered and washed to obtain a cake. The cake was repulped with water, heated to 95° C., stirred for two hours, filtered, washed (with water), and dried at 120° C. for 16 hours. Thus, particulate hexagonal plate-shaped zinc oxide was obtained.

Example 6

A slurry was obtained by repulping 79.2 g of starting particulate zinc oxide (FINEX-50 available from Sakai Chemical Industry Co., Ltd., particle size calculated from specific surface area: 0.02 μm) with 399 ml of water. Separately, 601 ml of a 1.30 mol/l aqueous solution of zinc acetate was prepared. To the aqueous solution was added 2.37 g of aluminum chloride hexahydrate (aluminum chloride: 1 mol % based on the starting particulate zinc oxide). The slurry and the zinc acetate aqueous solution were added simultaneously to 200 ml of water controlled at 30° C. such that the total amounts were added over 120 minutes. Thus, a slurry mixture containing a 0.65 mol/l aqueous solution of zinc acetate, the starting particulate zinc oxide, and aluminum chloride was obtained. Subsequently, the slurry mixture was heated to 95° C. over 65 minutes under stirring, and then aged at 95° C. for two hours under stirring. After the aging, the slurry mixture was immediately cooled and then filtered and washed to obtain a cake. The cake was repulped with water, heated to 95° C., stirred for two hours, filtered, washed (with water), and dried at 120° C. for 16 hours. Thus, particulate hexagonal plate-shaped zinc oxide was obtained.

Example 7

A slurry was obtained by repulping 79.6 g of starting particulate zinc oxide (FINEX-50 available from Sakai Chemical Industry Co., Ltd., particle size calculated from specific surface area: 0.02 μm) with 399 ml of water. Separately, 601 ml of a 1.30 mol/l aqueous solution of zinc acetate was prepared. To the aqueous solution was added 1.19 g of aluminum chloride hexahydrate (aluminum chloride: 0.5 mol % based on the starting particulate zinc oxide). The slurry and the zinc acetate aqueous solution were added simultaneously to 200 ml of water controlled at 30° C. such that the total amounts were added over 120 minutes. Thus, a slurry mixture containing a 0.65 mol/l aqueous solution of zinc acetate, the starting particulate zinc oxide, and aluminum chloride was obtained. Subsequently, the slurry mixture was heated to 95° C. over 65 minutes under stirring, and then aged at 95° C. for two hours under stirring. After the aging, the slurry mixture was immediately cooled and then filtered and washed to obtain a cake. The cake was repulped with water, heated to 95° C., stirred for two hours, filtered, washed (with water), and dried at 120° C. for 16 hours. Thus, particulate hexagonal plate-shaped zinc oxide was obtained.

Example 8

A slurry was obtained by repulping 78.4 g of starting particulate zinc oxide (FINEX-50 available from Sakai Chemical Industry Co., Ltd., particle size calculated from specific surface area: 0.02 μm) with 399 ml of water. Separately, 601 ml of a 1.30 mol/l aqueous solution of zinc acetate was prepared. To the aqueous solution was added 4.75 g of aluminum chloride hexahydrate (aluminum chloride: 2 mol % based on the starting particulate zinc oxide). The slurry and the zinc acetate aqueous solution were added simultaneously to 200 ml of water controlled at 30° C. such that the total amounts were added over 120 minutes. Thus, a slurry mixture containing a 0.65 mol/l aqueous solution of zinc acetate, the starting particulate zinc oxide, and aluminum chloride was obtained. Subsequently, the slurry mixture was heated to 95° C. over 65 minutes under stirring, and then aged at 95° C. for two hours under stirring. After the aging, the slurry mixture was immediately cooled and then filtered and washed to obtain a cake. The cake was repulped with water, heated to 95° C., stirred for two hours, filtered, washed (with water), and dried at 120° C. for 16 hours. Thus, particulate hexagonal plate-shaped zinc oxide was obtained.

Example 9

A slurry was obtained by repulping 80 g of starting particulate zinc oxide (FINEX-50 available from Sakai Chemical Industry Co., Ltd., particle size calculated from specific surface area: 0.02 μm) with 399 ml of water. Separately, 601 ml of a 1.30 mol/l aqueous solution of zinc acetate was prepared. To the aqueous solution was added 11.49 g of sodium chloride (sodium chloride: 20 mol % based on the starting particulate zinc oxide) and 0.07 g of aluminum chloride hexahydrate (aluminum chloride: 0.03 mol % based on the starting particulate zinc oxide). The slurry and the zinc acetate aqueous solution were added simultaneously to 200 ml of water controlled at 30° C. such that the total amounts were added over 120 minutes. Thus, a slurry mixture containing a 0.65 mol/l aqueous solution of zinc acetate, the starting particulate zinc oxide, and aluminum chloride was obtained. Subsequently, the slurry mixture was heated to 95° C. over 65 minutes under stirring, and then aged at 95° C. for two hours under stirring. After the aging, the slurry mixture was immediately cooled and then filtered and washed to obtain a cake. The cake was repulped with water, heated to 95° C., stirred for two hours, filtered, washed (with water), and dried at 120° C. for 16 hours. Thus, particulate hexagonal plate-shaped zinc oxide was obtained.

Comparative Example 1

A slurry was obtained by repulping 80 g of starting particulate zinc oxide (FINEX-50 available from Sakai Chemical Industry Co., Ltd., particle size calculated from specific surface area: 0.02 μm) with 399 ml of water. Separately, 601 ml of a 1.30 mol/l aqueous solution of zinc acetate was prepared. The slurry and the zinc acetate aqueous solution were added simultaneously to 200 ml of water controlled at 30° C. such that the total amounts were added over 120 minutes. Thus, a slurry mixture containing a 0.65 mol/l aqueous solution of zinc acetate and the starting particulate zinc oxide was obtained. Subsequently, the slurry mixture was heated to 95° C. over 65 minutes under stirring, and then aged at 95° C. for two hours under stirring. After the aging, the slurry mixture was immediately cooled and then filtered and washed to obtain a cake. The cake was repulped with water, heated to 95° C., stirred for two hours, filtered, washed (with water), and dried at 120° C. for 16 hours. Thus, particulate hexagonal plate-shaped zinc oxide was obtained.

Comparative Example 2

A slurry was obtained by repulping 78.4 g of starting particulate zinc oxide (FINEX-50 available from Sakai Chemical Industry Co., Ltd., particle size calculated from specific surface area: 0.02 μm) with 399 ml of water. Separately, 601 ml of a 1.30 mol/l aqueous solution of zinc acetate was prepared. To the aqueous solution was added 2.79 g of sodium sulfate (sodium sulfate: 2 mol % based on the starting particulate zinc oxide). The slurry and the zinc acetate aqueous solution were added simultaneously to 200 ml of water controlled at 30° C. such that the total amounts were added over 120 minutes. Thus, a slurry mixture containing a 0.65 mol/l aqueous solution of zinc acetate, the starting particulate zinc oxide, and the sodium sulfate was obtained. Subsequently, the slurry mixture was heated to 95° C. over 65 minutes under stirring, and then aged at 95° C. for two hours under stirring. After the aging, the slurry mixture was immediately cooled and then filtered and washed to obtain a cake. The cake was repulped with water, heated to 95° C., stirred for two hours, filtered, washed (with water), and dried at 120° C. for 16 hours. Thus, particulate hexagonal plate-shaped zinc oxide was obtained.

Comparative Example 3

A slurry was obtained by repulping 78.4 g of starting particulate zinc oxide (FINEX-50 available from Sakai Chemical Industry Co., Ltd., particle size calculated from specific surface area: 0.02 μm) with 399 ml of water. Separately, 601 ml of a 1.30 mol/l aqueous solution of zinc acetate was prepared. To the aqueous solution was added 2.60 g of ammonium sulfate (ammonium sulfate: 2 mol % based on the starting particulate zinc oxide). The slurry and the zinc acetate aqueous solution were mixed into 200 ml of water controlled at 30° C. such that the total amounts were added over 120 minutes. Thus, a slurry mixture containing a 0.65 mol/l aqueous solution of zinc acetate, the starting particulate zinc oxide, and the ammonium sulfate was obtained. Subsequently, the slurry mixture was heated to 95° C. over 65 minutes under stirring, and then aged at 95° C. for two hours under stirring. After the aging, the slurry mixture was immediately cooled and then filtered and washed to obtain a cake. The cake was repulped with water, heated to 95° C., stirred for two hours, filtered, washed (with water), and dried at 120° C. for 16 hours. Thus, particulate hexagonal plate-shaped zinc oxide was obtained.

Comparative Example 4

A slurry was obtained by repulping 78.4 g of starting particulate zinc oxide (FINEX-50 available from Sakai Chemical Industry Co., Ltd., particle size calculated from specific surface area: 0.02 μm) with 399 ml of water. Separately, 601 ml of a 1.30 mol/l aqueous solution of zinc acetate was prepared. To the aqueous solution was added 1.67 g of sodium nitrate (sodium nitrate: 2 mol % based on the starting particulate zinc oxide). The slurry and the zinc acetate aqueous solution were added simultaneously to 200 ml of water controlled at 30° C. such that the total amounts were added over 120 minutes. Thus, a slurry mixture containing a 0.65 mol/l aqueous solution of zinc acetate, the starting particulate zinc oxide, and the sodium nitrate was obtained. Subsequently, the slurry mixture was heated to 95° C. over 65 minutes under stirring, and then aged at 95° C. for two hours under stirring. After the aging, the slurry mixture was immediately cooled and then filtered and washed to obtain a cake. The cake was repulped with water, heated to 95° C., stirred for two hours, filtered, washed (with water), and dried at 120° C. for 16 hours. Thus, particulate hexagonal plate-shaped zinc oxide was obtained.

Comparative Example 5

A slurry was obtained by repulping 76.8 g of starting particulate zinc oxide (FINEX-50 available from Sakai Chemical Industry Co., Ltd., particle size calculated from specific surface area: 0.02 μm) with 399 ml of water. Separately, 601 ml of a 1.30 mol/l aqueous solution of zinc acetate was prepared. To the aqueous solution was added 4.17 g of sodium carbonate (sodium carbonate: 4.2 mol % based on the starting particulate zinc oxide). The slurry and the zinc acetate aqueous solution were added simultaneously to 200 ml of water controlled at 30° C. such that the total amounts were added over 120 minutes. Thus, a slurry mixture containing a 0.65 mol/l aqueous solution of zinc acetate, the starting particulate zinc oxide, and the sodium carbonate was obtained. Subsequently, the slurry mixture was heated to 95° C. over 65 minutes under stirring, and then aged at 95° C. for two hours under stirring. After the aging, the slurry mixture was immediately cooled and then filtered and washed to obtain a cake. The cake was repulped with water, heated to 95° C., stirred for two hours, filtered, washed (with water), and dried at 120° C. for 16 hours. Thus, particulate hexagonal plate-shaped zinc oxide was obtained.

Evaluation of Physical Properties of Particulate Zinc Oxide

The physical properties of the particulate zinc oxides produced in Examples 1 to 9 and Comparative Examples 1 to 5 were measured. The results are shown in Table 1.

Figure 1:
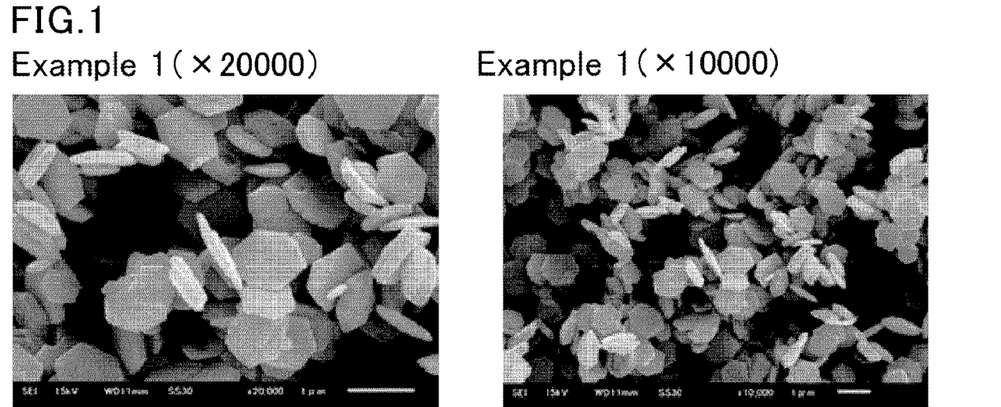
FIG. 1 shows an electron micrograph of particulate hexagonal plate-shaped zinc oxide obtained in Example 1.
Figure 2:
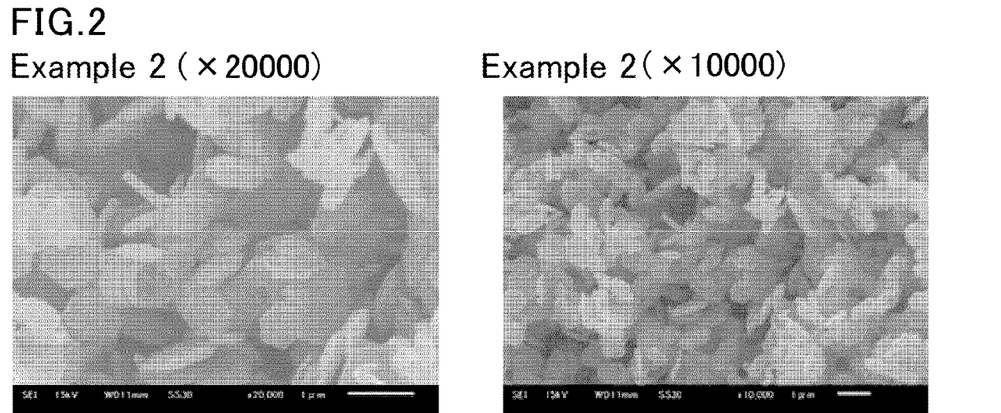
FIG. 2 shows an electron micrograph of particulate hexagonal plate-shaped zinc oxide obtained in Example 2.
Figure 3:
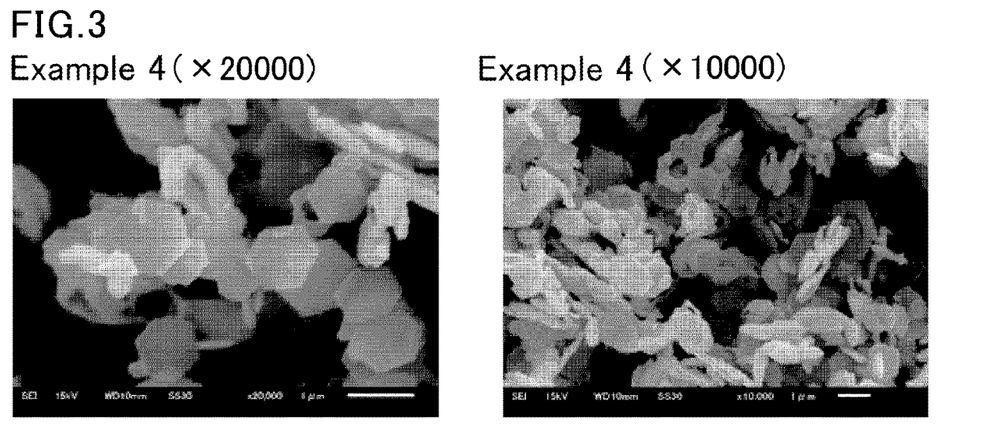
FIG. 3 shows an electron micrograph of particulate hexagonal plate-shaped zinc oxide obtained in Example 4.
Figure 4:
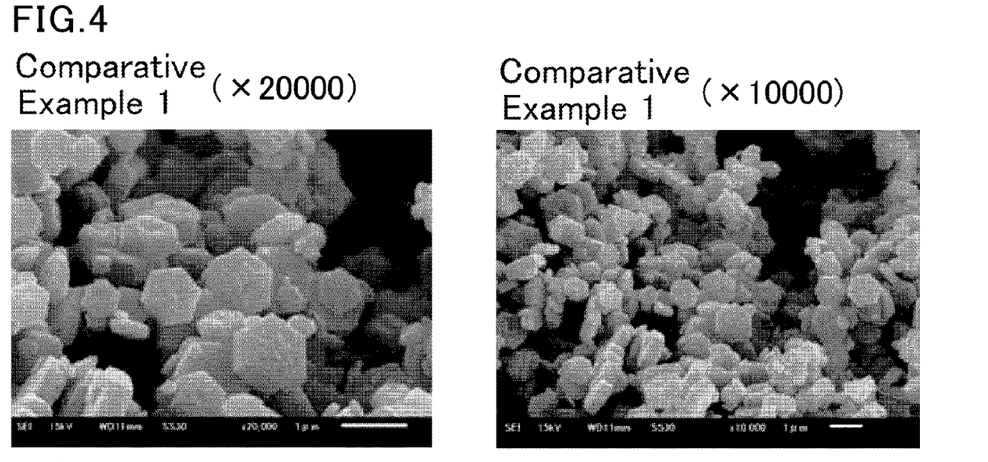
FIG. 4 shows an electron micrograph of particulate hexagonal plate-shaped zinc oxide obtained in Comparative Example 1.
Figure 5:
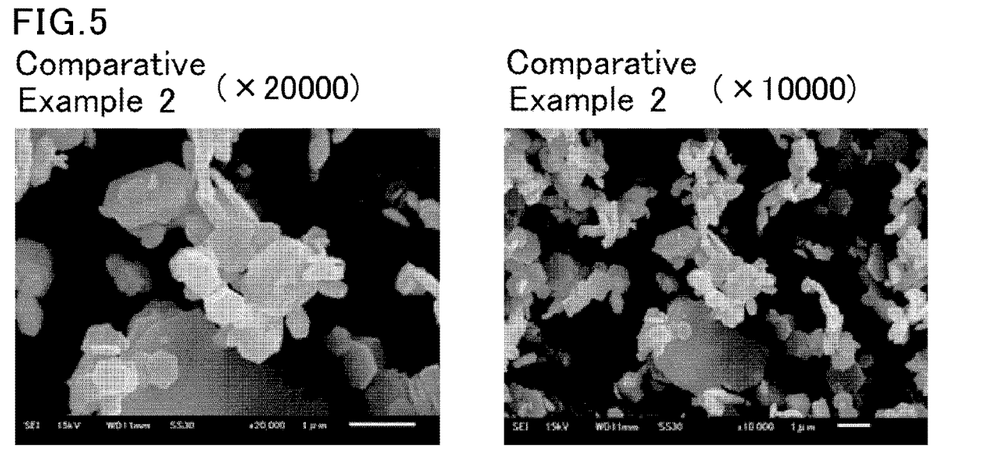
FIG. 5 shows an electron micrograph of particulate hexagonal plate-shaped zinc oxide obtained in Comparative Example 2.
Figure 6:
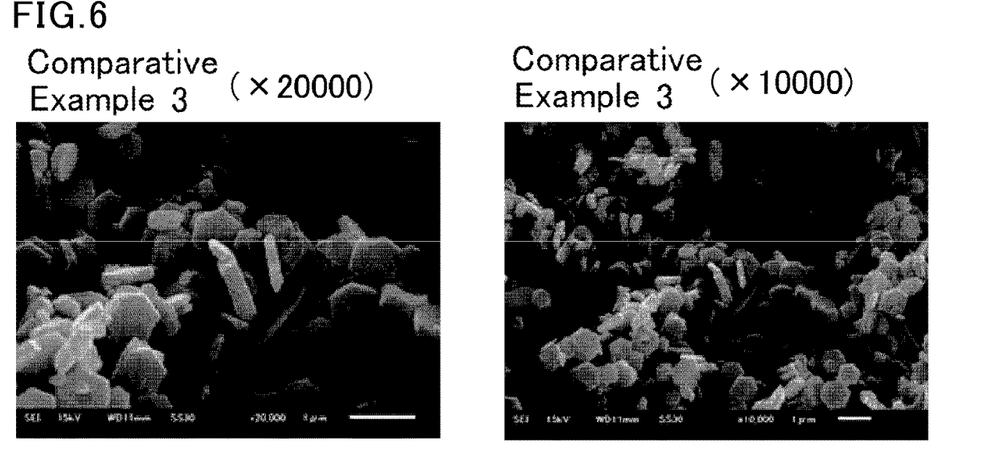
FIG. 6 shows an electron micrograph of particulate hexagonal plate-shaped zinc oxide obtained in Comparative Example 3.
Figure 7:
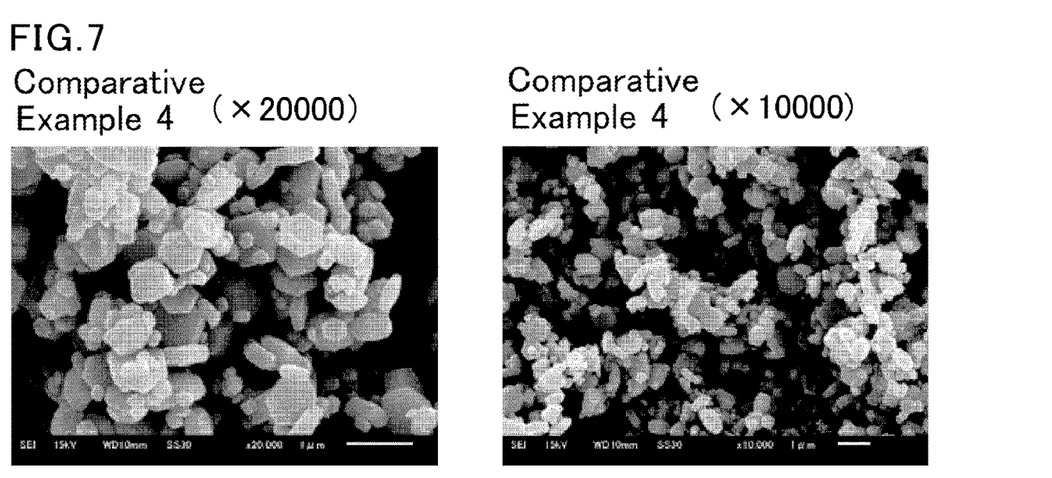
FIG. 7 shows an electron micrograph of particulate hexagonal plate-shaped zinc oxide obtained in Comparative Example 4.
Figure 8:
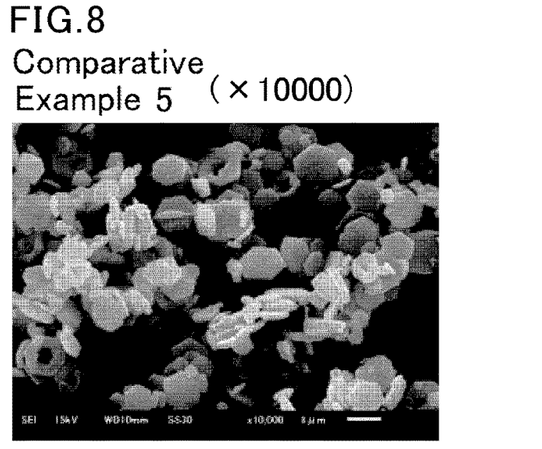
FIG. 8 shows an electron micrograph of particulate hexagonal plate-shaped zinc oxide obtained in Comparative Example 5.

The electron micrographs of the particulate zinc oxides produced in Examples 1, 2, and 4 and Comparative Examples 1 to 5 were taken with a scanning electron microscope JSM-6510A (JEOL Ltd.). They are shown in FIGS. 1 to 8.

<Particle Shape>

The particle shape was observed in a scanning electron microscope JSM-6510A (JEOL Ltd.).

<Aspect Ratio>

In the micrographs at magnifications of 2000× to 50000× taken with a scanning electron microscope JSM-6510A (JEOL Ltd.), the aspect ratio was determined as a ratio of L/T where L is an average of measured particle diameters (μm) of 100 hexagonal plate-shaped zinc oxide particles, the particle diameter being the diagonal diameter of the frontal image of the hexagonal plate-shaped surface of a hexagonal plate-shaped zinc oxide particle (the length of any one of three diagonal lines of the hexagonal plate-shaped surface of a hexagonal plate-shaped zinc oxide particle), and T is an average of measured thickness (μm) of 100 hexagonal plate-shaped zinc oxide particles, the thickness being the shorter length of the frontal image of the side face of a hexagonal plate-shaped zinc oxide particle (apparently rectangular particle).

<D10, D50 (Median Diameter), D90>

In the micrographs at magnifications of 2000× to 50000× taken with a scanning electron microscope JSM-6510A (JEOL Ltd.), the particle diameters (μm) of 100 hexagonal plate-shaped zinc oxide particles in the SEM image were measured. Here, the particle diameter is the diagonal diameter (the length of any one of three diagonal lines of the hexagonal plate-shaped surface of a hexagonal plate-shaped zinc oxide particle). The cumulative distribution of the particle diameters was calculated.

The particle size at which 10% by number of particles were accumulated was expressed by D10, the particle size at which 50% by number of particles were accumulated was expressed by D50, and the particle size at which 90% by number of particles were accumulated was expressed by D90.

<BET Specific Surface Area>

The BET specific surface area ($m^2/g$) was determined with a fully automatic BET specific surface area measuring apparatus Macsorb (Mountech Co., Ltd.).

<Total Light Transmittance at 350 nm, Parallel Light Transmittance at 400 nm>

The total light transmittance at 350 nm and the parallel light transmittance at 400 nm were values determined using a spectrophotometer (V-570 available from JASCO Corporation). Specifically, 2 g of the particulate zinc oxide obtained in each of the examples and the comparative examples, 10 g of acrylic polyol resin, 5 g of xylene, 5 g of butyl acetate, and 38 g of 1.5 mmφ glass beads were put into a 75 ml mayonnaise bottle and shaken in a paint conditioner for 90 minutes to prepare a dispersion. The dispersion was applied to a glass slide with a bar coater #6 and subjected to measurement of the total light transmittance at a wavelength of 350 nm and the parallel light transmittance at a wavelength of 400 nm using a spectrophotometer (V-570 available from JASCO Corporation).

<Texture>

The powder texture is an indicator of slippage and roughness of powder when a small amount of a powder was placed on the skin and drawn by a finger. Each sample was evaluated on a ten-point scale (1 to 10). A higher score indicates better slippage with no roughness, and a lower score indicates poorer slippage with roughness. The powder of Comparative Example 1 was defined as a standard (score 5).

TABLE 1

| | | | Example 1 | Example 2 | Example 3 | Example 4 | Example 5 | Example 6 | Example 7 |
|---|---|---|---|---|---|---|---|---|---|
| Conditions of preparation | Starting zinc oxide (material) slurry | Zinc oxide as material | FINEX-50 | FINEX-50 | FINEX-50 | FINEX-50 | FINEX-50 | FINEX-50 | FINEX-50 |
| | | Particle size of material (μm) | 0.02 | 0.02 | 0.02 | 0.02 | 0.02 | 0.02 | 0.02 |
| | | Amount of material used (g) | 78.4 | 78.4 | 76.8 | 64 | 76.8 | 79.2 | 79.6 |
| | | Amount of water for repulping of material (ml) | 399 | 399 | 399 | 399 | 399 | 399 | 399 |
| | Zinc salt aqueous solution | Type | Zinc acetate aqueous solution | Zinc acetate aqueous solution | Zinc acetate aqueous solution | Zinc acetate aqueous solution | Zinc acetate aqueous solution | Zinc acetate aqueous solution | Zinc acetate aqueous solution |
| | | Concentration (mol/l) | 1.3 | 1.3 | 1.3 | 1.3 | 1.3 | 1.3 | 1.3 |
| | | Amount (ml) | 601 | 601 | 601 | 601 | 601 | 601 | 601 |
| | Substance 1 added | Type | Sodium chloride | Ammonium chloride | Sodium chloride | Sodium chloride | Lithium chloride | Aluminum chloride hexahydrate | Aluminum chloride hexahydrate |
| | | Amount (g) | 1.15 | 1.05 | 2.30 | 11.49 | 1.67 | 2.37 | 1.19 |
| | | Amount of chloride (mol %), etc., relative to starting zinc oxide | 2.0 | 2.0 | 4.2 | 25 | 4.2 | 1 | 0.5 |
| | Substance 2 added | Type | | | | | | | |
| | | Amount (g) | | | | | | | |
| | | Amount of chloride (mol %), etc., relative to starting zinc oxide | | | | | | | |
| | | Mixing time (min) | 120 | 120 | 120 | 120 | 120 | 120 | 120 |
| | | Mixing temperature (° C.) | 30 | 30 | 30 | 30 | 30 | 30 | 30 |
| | | Concentration of zinc acetate in aqueous solution (mol/l) after mixing | 0.65 | 0.65 | 0.65 | 0.65 | 0.65 | 0.65 | 0.65 |
| | | Aging temperature (° C.) | 95 | 95 | 95 | 95 | 95 | 95 | 95 |
| | | Aging time (Hr) | 2 | 2 | 2 | 2 | 2 | 2 | 2 |
| Properties of particle | | Composition of obtained particle | Zinc oxide | Zinc oxide | Zinc oxide | Zinc oxide | Zinc oxide | Zinc oxide | Zinc oxide |
| | | Shape of obtained particle | Hexagonal plate shape | Hexagonal plate shape | Hexagonal plate shape | Hexagonal plate shape | Hexagonal plate shape | Hexagonal plate shape | Hexagonal plate shape |
| | | Aspect ratio | 6.0 | 4.7 | 5.3 | 6.4 | 4.7 | 5.3 | 5.2 |
| | | D10 (μm) | 0.54 | 0.43 | 0.49 | 0.59 | 0.37 | 0.50 | 0.48 |
| | | Median diameter D50 (μm) | 0.77 | 0.70 | 0.70 | 0.85 | 0.61 | 0.71 | 0.78 |
| | | D90 (μm) | 0.97 | 0.90 | 0.94 | 1.23 | 0.77 | 0.87 | 1.00 |
| | | D90/D10 | 1.8 | 2.1 | 1.9 | 2.1 | 2.1 | 1.7 | 2.1 |
| | | BET specific surface area (m$^2$/g) | 3.2 | 3.2 | 3.1 | 4.2 | 3.9 | 4.8 | 3.4 |
| | | Total light transmittance (%) at 350 nm | 56.29 | 56.86 | 57.59 | 53.38 | 45.94 | 57.92 | 57.37 |
| | | Parallel light transmittance (%) at 400 nm | 30.90 | 29.87 | 31.15 | 30.82 | 23.92 | 33.86 | 29.73 |
| | | Texture | 8 | 8 | 8 | 9 | 8 | 8 | 8 |

| | | | Example 8 | Example 9 | Comparative Example 1 | Comparative Example 2 | Comparative Example 3 | Comparative Example 4 | Comparative Example 5 |
|---|---|---|---|---|---|---|---|---|---|
| Conditions of preparation | Starting zinc oxide (material) slurry | Zinc oxide as material | FINEX-50 | FINEX-50 | FINEX-50 | FINEX-50 | FINEX-50 | FINEX-50 | FINEX-50 |
| | | Particle size of material (μm) | 0.02 | 0.02 | 0.02 | 0.02 | 0.02 | 0.02 | 0.02 |
| | | Amount of material used (g) | 78.4 | 80 | 80 | 78.4 | 78.4 | 78.4 | 76.8 |
| | | Amount of water for repulping of material (ml) | 399 | 399 | 399 | 399 | 399 | 399 | 399 |

TABLE 1-continued

| | | | | | | | | |
|---|---|---|---|---|---|---|---|---|
| | Zinc salt aqueous solution | Type | Zinc acetate aqueous solution | Zinc acetate aqueous solution | Zinc acetate aqueous solution | Zinc acetate aqueous solution | Zinc acetate aqueous solution | Zinc acetate aqueous solution | Zinc acetate aqueous solution |
| | | Concentration (mol/l) | 1.3 | 1.3 | 1.3 | 1.3 | 1.3 | 1.3 | 1.3 |
| | | Amount (ml) | 601 | 601 | 601 | 601 | 601 | 601 | 601 |
| | Substance 1 added | Type | Aluminum chloride hexahydrate | Sodium chloride | | Sodium sulfate | Ammonium sulfate | Sodium nitrate | Sodium carbonate |
| | | Amount (g) | 4.75 | 11.49 | | 2.79 | 2.60 | 1.67 | 4.17 |
| | | Amount of chloride (mol %), etc., relative to starting zinc oxide | 2 | 20 | | 2 | 2 | 2 | 4.2 |
| | Substance 2 added | Type | | Aluminum chloride hexahydrate | | | | | |
| | | Amount (g) | | 0.07 | | | | | |
| | | Amount of chloride (mol %), etc., relative to starting zinc oxide | | 0.03 | | | | | |
| | Mixing time (min) | | 120 | 120 | 120 | 120 | 120 | 120 | 120 |
| | Mixing temperature (° C.) | | 30 | 30 | 30 | 30 | 30 | 30 | 30 |
| | Concentration of zinc acetate in aqueous solution (mol/l) after mixing | | 0.65 | 0.65 | 0.65 | 0.65 | 0.65 | 0.65 | 0.65 |
| | Aging temperature (° C.) | | 95 | 95 | 95 | 95 | 95 | 95 | 95 |
| | Aging time (Hr) | | 2 | 2 | 2 | 2 | 2 | 2 | 2 |
| Properties of particle | Composition of obtained particle | | Zinc oxide | Zinc oxide | Zinc oxide | Zinc oxide | Zinc oxide | Zinc oxide | Zinc oxide |
| | Shape of obtained particle | | Hexagonal plate shape | Hexagonal plate shape | Hexagonal plate shape | Hexagonal plate shape | Hexagonal plate shape | Hexagonal plate shape | Hexagonal plate shape |
| | Aspect ratio | | 5.2 | 12.7 | 2.8 | 3.3 | 3.3 | 2.1 | 3.0 |
| | D10 (μm) | | 0.47 | 0.90 | 0.33 | 0.36 | 0.31 | 0.16 | 0.36 |
| | Median diameter D50 (μm) | | 0.79 | 1.11 | 0.64 | 0.54 | 0.51 | 0.37 | 0.63 |
| | D90 (μm) | | 0.95 | 1.22 | 0.99 | 0.87 | 0.78 | 0.69 | 0.99 |
| | D90/D10 | | 2.0 | 1.4 | 3.0 | 2.4 | 2.5 | 4.2 | 2.8 |
| | BET specific surface area (m$^2$/g) | | 6.0 | 5.1 | 2.0 | 3.4 | 3.4 | 2.8 | 3.4 |
| | Total light transmittance (%) at 350 nm | | 53.62 | 31.58 | 68.99 | 55.50 | 57.90 | 57.52 | 66.67 |
| | Parallel light transmittance (%) at 400 nm | | 32.00 | 8.11 | 41.22 | 29.76 | 30.05 | 31.19 | 39.46 |
| | Texture | | 8 | 9 | 5 | 7 | 7 | 7 | 7 |

The invention claimed is:

1. A method for producing hexagonal plate-shaped zinc oxide, the method comprising:
   a step (1) of preparing a slurry mixture containing starting particulate zinc oxide, a zinc acetate solution, and a chloride that is at least one selected from the group consisting of sodium chloride, ammonium chloride, and lithium chloride; and
   a step (2) of heat aging the slurry mixture obtained in the step (1) at 60° C. to 100° C.

2. The method for producing hexagonal plate-shaped zinc oxide according to claim 1,
   wherein the chloride is present in an amount of 0.3 mol % or more based on the starting particulate zinc oxide used in the step (1) in the slurry mixture obtained in the step (1).

3. The method for producing hexagonal plate-shaped zinc oxide according to claim 1, the method further comprising a step (3) of washing solids obtained from a slurry reaction product produced in the step (2) with water having a temperature from 70° C. to below 100° C.

* * * * *